US011793415B1

(12) United States Patent
Xie (10) Patent No.: US 11,793,415 B1
(45) Date of Patent: Oct. 24, 2023

(54) METHOD, APPARATUS AND SYSTEM FOR MONITORING HEART RATE IN SLEEP STATE BASED ON MICROWAVE RADAR

(71) Applicant: Yihuiyun Intelligent Technology (Shenzhen) Co., Ltd., Shenzhen (CN)

(72) Inventor: Jun Xie, Guangdong (CN)

(73) Assignee: Yihuiyun Intelligent Technology (Shenzhen) Co., Ltd., Shenzhen (CN)

(*) Notice: Subject to any disclaimer, the term of this patent is extended or adjusted under 35 U.S.C. 154(b) by 0 days.

(21) Appl. No.: 18/170,550

(22) Filed: Feb. 17, 2023

(30) Foreign Application Priority Data

Jun. 13, 2022 (CN) .......................... 202210659363.0

(51) Int. Cl.
    *A61B 5/00* (2006.01)
    *A61B 5/024* (2006.01)
    *G01S 7/41* (2006.01)
    *A61B 5/0507* (2021.01)
    *A61B 5/0205* (2006.01)
    *A61B 5/08* (2006.01)

(52) U.S. Cl.
    CPC ........ *A61B 5/02444* (2013.01); *A61B 5/0205* (2013.01); *A61B 5/0507* (2013.01); *A61B 5/4809* (2013.01); *A61B 5/741* (2013.01); *A61B 5/746* (2013.01); *G01S 7/415* (2013.01); *A61B 5/0816* (2013.01)

(58) Field of Classification Search
    CPC . A61B 5/02444; A61B 5/0205; A61B 5/0507; A61B 5/4809; A61B 5/741; A61B 5/746; A61B 5/0816; G01S 7/415
    See application file for complete search history.

(56) References Cited

U.S. PATENT DOCUMENTS

2007/0282212 A1   12/2007   Sierra et al.
2021/0000384 A1   1/2021    Jarchi et al.

FOREIGN PATENT DOCUMENTS

| CN | 106073717 A | 11/2016 |
| CN | 106175770 A | 12/2016 |
| CN | 108523901 A | 9/2018 |
| CN | 111481207 A | 8/2020 |

(Continued)

OTHER PUBLICATIONS

Hao Niu, his Dissertation for the Master Degree, title "Research on Home Non-contact Vital Sign Monitoring System Based on Doppler Radar" published on Dec. 2020, China.

*Primary Examiner* — Rex R Holmes
(74) *Attorney, Agent, or Firm* — Andrew C. Cheng (57) ABSTRACT

The present invention relates to a method for monitoring a heart rate in a sleep state based on a microwave radar. The method includes: controlling the microwave radar to send a first detection signal to the human body when the microwave radar detects that the human body is not moving, and extracting a respiration waveform signal from the returned first detection signal; comparing the similarity of the respiration waveform signal and at least one respiration waveform signal standard sample in a sleep state in a preset respiration waveform signal database to obtain a similarity comparison result; determining that an object to be detected is currently in the sleep state and controlling the microwave radar to send a second detection signal to the object; and extracting a heart rate waveform signal from the returned second detection signal, and calculating a heart rate according to the heart rate waveform signal.

11 Claims, 3 Drawing Sheets

(56) References Cited

FOREIGN PATENT DOCUMENTS

| | | |
|---|---|---|
| CN | 113367666 A | 9/2021 |
| CN | 113448438 A | 9/2021 |
| CN | 113925475 A | 1/2022 |
| CN | 114176564 A | 3/2022 |
| EP | 1551286 A2 | 7/2005 |

METHOD, APPARATUS AND SYSTEM FOR MONITORING HEART RATE IN SLEEP STATE BASED ON MICROWAVE RADAR

FIELD OF THE INVENTION

The present invention relates to the technical field of health detection, in particular to a method, apparatus and system for monitoring a heart rate in a sleep state based on a microwave radar.

BACKGROUND OF THE INVENTION

The heart rate is generally defined as the number of beats per minute of the human heart and changes in heart rate are closely related to heart diseases. Therefore, it is very important to know your heart rate status in time as soon as possible when the heart rate is abnormal, in order to perform treatment for pathogenesis. In the prior art, people often monitor the user's heart rate through wearable devices such as bracelets and smart watches. However, it is difficult for users to know exactly when they start monitoring their heart rates after falling asleep, making it difficult for users to accurately understand their heart rate health during sleep. In addition, existing heart rate monitoring methods require users to wear these devices during sleep, thereby failing to achieve non-contact monitoring.

SUMMARY OF THE INVENTION

Embodiments of the present invention provide a method, apparatus and system for monitoring a heart rate in a sleep state based on a microwave radar, which can perform non-contact monitoring on the heart rate after a user enters the sleep state, such that the user understands the heart rate health in his/her sleep state.

An embodiment of the present invention provides a method for monitoring a heart rate in a sleep state based on a microwave radar. The method includes:
  controlling the microwave radar to regularly send ranging signals to surrounding objects to be detected, and calculating a distance between the microwave radar and the object to be detected based on a returned ranging signal;
  controlling the microwave radar to send a first detection signal to the object to be detected when a difference between the currently calculated distance and a distance calculated at the previous moment is less than a preset distance difference;
  extracting a respiration waveform signal from the returned first detection signal;
  comparing the similarity of the respiration waveform signal and at least one respiration waveform signal standard sample in a sleep state in a preset respiration waveform signal database to obtain a similarity comparison result;
  determining that an object to be detected is currently in the sleep state if a similarity, value in the similarity comparison result is greater than a preset similarity threshold; and
  controlling the microwave radar to send a second detection signal to the object to be detected, extracting a heart rate waveform signal from the returned second detection signal, and calculating and recording a heart rate according to the heart rate waveform signal, till the next ranging signal needs to be sent.

As an improvement of the present application, said comparing the similarity of the respiration waveform signal and at least one respiration waveform signal standard sample in the sleep state in the preset respiration waveform signal database to obtain the similarity comparison result comprises:
  determining a target waveform segment of a preset length from the respiration waveform signal;
  performing sliding interception on the target waveform segment according to a preset interception frame width, and calculating a ratio of an amplitude difference between a maximum amplitude and a minimum amplitude of the waveform segment in each interception frame to a width of the interception frame as a first ratio of each interception frame of the target waveform segment;
  performing sliding interception on the respiration waveform signal standard sample in each sleep state in the preset respiration waveform signal database according to the preset interception frame width, and calculating a ratio of an amplitude difference between a maximum amplitude and a minimum amplitude of a waveform segment in each interception frame to the width of the interception frame as a second ratio of each interception frame of the respiration waveform signal standard sample, a waveform length of each respiration waveform signal standard sample being the preset length; and
  calculating the similarity of the target waveform segment and each respiration waveform signal standard sample in the respiration waveform signal database by using a similarity algorithm based on the first ratio of each interception frame of the target waveform segment and the second ratio of the corresponding interception frame of each respiration waveform signal standard sample.

As an improvement of the present application, the similarity algorithm is as follows:

$$w_{AB} = \frac{1}{1+d}$$

wherein $w_{AB}$ is the similarity; d is a distance of the similarity, $$d = \sqrt{\sum_{i=1}^{n}(x_i - y_i)^2};$$

$x_i$ is a first ratio of the $i^{th}$ interception frame of the target waveform segment; $y_i$ is a second ratio of the $i^{th}$ interception frame of each respiration waveform signal standard sample; and n is the number of intercepted interception frames.

As an improvement of the present application, after calculating the heart rate according to the heart rate waveform signal, the method further includes:
  judging whether the calculated heart rate exceeds a preset heart rate safety value range;
  determining that a heart health status of the object to be detected is an abnormal heart rate if the calculated heart rate exceeds the preset heart rate safety value range; and
  determining that the heart health status of the object to be detected is a normal heart rate if the calculated heart rate does not exceed the preset heart rate safety value range.

As an improvement of the present application, after determining that the heart health status of the object to be detected is the abnormal heart rate, the method further includes:

sending prompt information to a user terminal or controlling a voice prompt apparatus to send a warning sound to the user.

Another embodiment of the present invention correspondingly provides an apparatus for monitoring a heart rate in a sleep state based on a microwave radar. The apparatus includes:

a first controlling module, configured to control the microwave radar to regularly, send ranging signals to surrounding objects to be detected, and calculating a distance between the microwave radar and the object to be detected based on a returned ranging signal;

a second controlling module, configured to control the microwave radar to send a first detection signal to the object to be detected when a difference between the currently, calculated distance and a distance calculated at, the previous moment is less than a preset distance difference;

a first signal extracting module, configured to extract a respiration waveform signal from the returned first detection signal;

a similarity comparing module, configured to compare the similarity of the respiration waveform signal and at least one respiration waveform signal standard sample in a sleep state in a preset respiration waveform signal database to obtain a similarity comparison result;

a judging module, configured to judge that an object to be detected is currently in the sleep state if a similarity value in the similarity comparison result is greater than a preset similarity threshold; and a third controlling module, configured to control the microwave radar to send a second detection signal to the object to be detected, extract a heart rate waveform signal from the returned second detection signal, and calculate and record a heart rate according to the heart rate waveform signal, till the next ranging signal needs to be sent.

As an improvement of the present application, the similarity comparing module is specifically configured to:

determine a target waveform segment of a preset length from the respiration waveform signal;

perform sliding interception on the target waveform segment according to a preset interception frame width, and calculate a ratio of an amplitude difference between a maximum amplitude and a minimum amplitude of the waveform segment in each interception frame to a width of the interception frame as a first ratio of each interception frame of the target waveform segment;

perform sliding interception on the respiration waveform signal standard sample in each sleep state in the preset respiration waveform signal database according to the preset interception frame width, and calculate a ratio of an amplitude difference between a maximum amplitude and a minimum amplitude of the waveform segment in each interception frame to the width of the interception frame as a second ratio of each interception frame of the respiration waveform signal standard sample, a waveform length of each respiration waveform signal standard sample being the preset length; and calculate the similarity of the target waveform segment and each respiration waveform signal standard sample in the respiration waveform signal database by using a similarity algorithm based on the first ratio of each interception frame of the target waveform segment and the second ratio of the corresponding interception frame of each respiration waveform signal standard sample.

As an improvement of the present application, the apparatus further includes:

a judging module; configured to judge whether the calculated heart rate exceeds a preset heart rate safety value range;

a first determining module, configured to determine that a heart health status of the object to be detected is an abnormal heart rate if the calculated heart rate exceeds the preset heart rate safety value range; and a second determining module, configured to determine that the heart health status of the object to be detected is a normal heart rate if the calculated heart rate does not exceed the preset heart rate safety value range.

Another embodiment of the present invention provides a system for monitoring a heart rate in a sleep state based on a microwave radar. The system includes a processor, a memory, and a computer program that is stored in the memory and configured to be executed by the processor, wherein the processor is configured to implement the method for monitoring the heart rate in the sleep state based on the microwave radar according to the above embodiment of the present invention when executing the computer program.

Another embodiment of the present invention provides a storage medium. The computer-readable storage medium includes a computer program stored therein, wherein the computer program, when in operation, controls a device where the computer-readable storage medium is located to perform the method for monitoring the heart rate in the sleep state based on the microwave radar according to the above embodiment of the present invention.

Compared with the prior art, one of the above technical solutions has the following advantages:

controlling the microwave radar to send a first detection signal to an object to be detected when the microwave radar detects that the object to be detected is not moving, and extracting a respiration waveform signal from the returned first detection signal; comparing the similarity of the respiration waveform signal and at least one respiration waveform signal standard sample in a sleep state in a preset respiration waveform signal database to obtain a similarity comparison result; judging that the object to be detected is currently in the sleep state if a similarity value in the similarity comparison result is greater than a preset similarity threshold, and controlling the microwave radar to send a second detection signal to the object to be detected; and extracting a heart rate waveform signal from the returned second detection signal, and calculating and recording a heart rate according to the heart rate waveform signal. It can thus be seen that the method, apparatus and system of the embodiments can perform non-contact monitoring on the heart rate after a user enters the sleep state, such that the user understands the heart rate health in his/her sleep state. Of course, the implementation of any product of the present invention does not necessarily need to achieve all the advantages described above at the same time.

DETAILED DESCRIPTIONS OF THE INVENTION

The technical solutions in the embodiments of the present invention will be described clearly and completely in conjunction with the accompanying drawings in the embodiments of the present invention. Apparently, the described embodiments are merely some embodiments, rather than all embodiments, of the present invention. Based on the embodiments of the present invention, all other embodiments derived by a person of ordinary skill in the art without creative efforts shall fail within the protection scope of the present invention.

Figure 1:
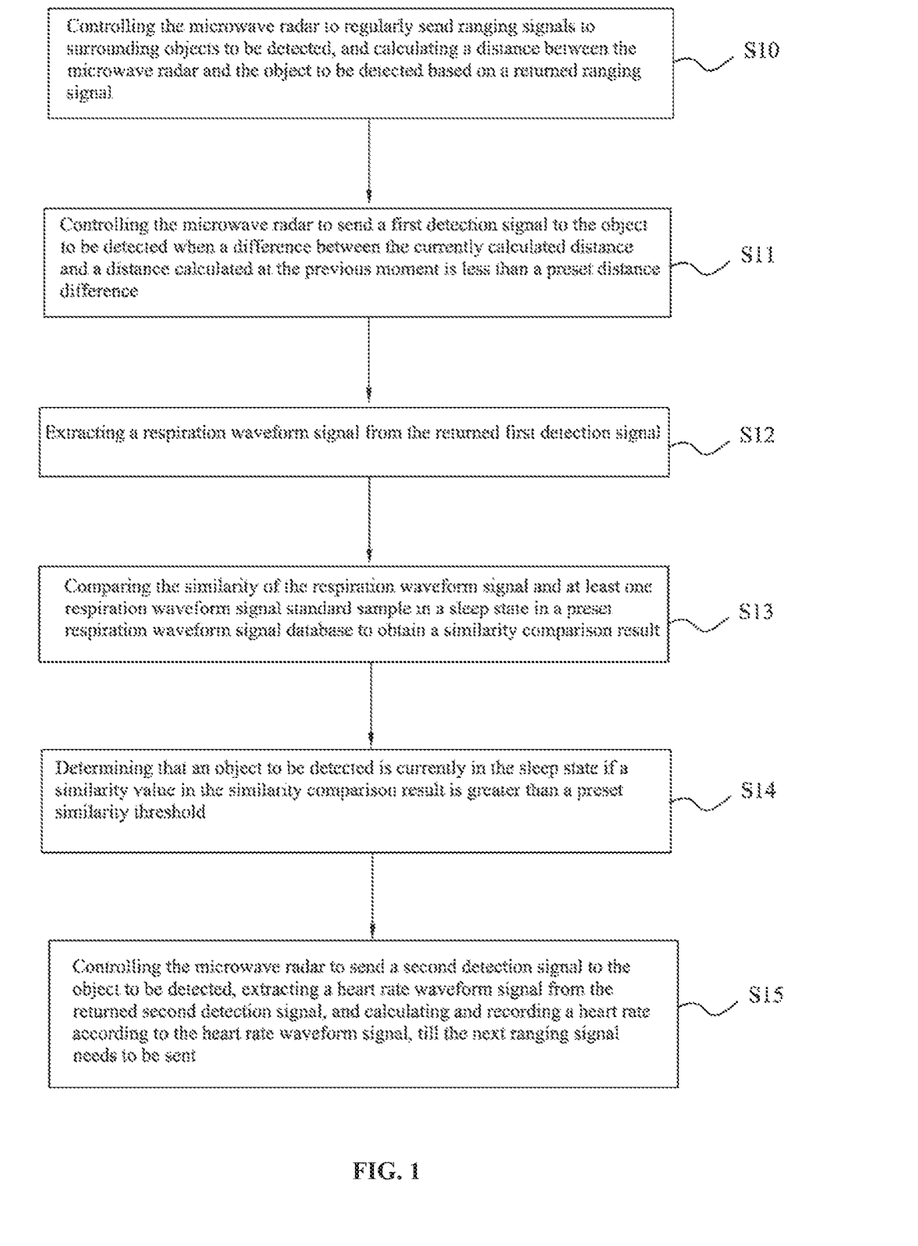
FIG. 1 is a schematic flowchart of a method for monitoring a heart rate in a sleep state based on a microwave radar according to an embodiment of the present invention.

FIG. 1 is a schematic flowchart of a method for monitoring a heart rate in a sleep state based on a microwave radar according to an embodiment of the present invention. The method may be performed by a system for monitoring a heart rate in a sleep state based on a microwave radar. The method includes the following steps S10 to S15.

In S10, the microwave radar is controlled to regularly send ranging signals to surrounding objects to be detected, and a distance between the microwave radar and the object to be detected is calculated based on the returned ranging signal.

The distance can be calculated by means of ranging such as a signal phase offset of the returned ranging signal, which will not be repeated here. It may be understood that a sending time interval of two sequential ranging signals is fixed in advance and cannot be too short, and the power consumption of signal transmission can be increased if the sending time interval is too short, which is not convenient for subsequent heart rate monitoring; but the sending time interval should not be too long, and it is difficult to detect in time whether the user has entered the sleep state if the sending time interval is too long. Exemplarily, the sending time interval may be 10-30 seconds, specifically, 15 seconds.

In S11, the microwave radar is controlled to send a first detection signal to the object to be detected when a difference between the currently calculated distance and a distance calculated at the previous moment is less than a preset distance difference, till the next ranging signal needs to be sent.

Specifically, when the difference between the currently calculated distance and the distance calculated at the previous moment is less than the preset distance difference, it is indicated that the current user is in a still state, may be in a state of just falling asleep, or may be in a state of waking but the human body is still lying down without moving. Therefore, it is necessary to further analyze if the user is falling asleep. At this time, the microwave radar is controlled to send the first detection signal to the object to be detected.

In S12, a respiration waveform signal is extracted from a returned first detection signal.

Exemplarily, the respiration waveform signal may be extracted from the returned first detection signal by means of a phase demodulation principle of radar.

In S13, the similarity of the respiration waveform signal and at least one respiration waveform signal standard sample in a sleep state in a preset respiration waveform signal database is compared to obtain a similarity comparison result.

A plurality of respiration waveform signal standard samples in the sleep state is pre-stored in the respiration waveform signal database. These respiration waveform signal standard samples are collected in advance from different groups of people who just enter the sleep state, and waveform lengths of these respiration waveform signal standard samples are equal. It may be understood that the human body respiration is thoracic respiration in an awake state, and is abdominal respiration in an asleep state. The thoracic respiration allows the human body to take a breath more efficiently, and is more suitable for supplementation when a large amount of oxygen is consumed in the awake state. The frequency of human body respiration in the awake state is faster than that of the human body respiration in the sleep state, and the human body respiration in the sleep state is relatively more uniform. Therefore, the human respiration waveform signal in the sleep state is different from the human body respiration waveform signal in the awake state.

In S14, it is determined that the object to be detected is currently in the sleep state if a similarity value in the similarity comparison result is greater than a preset similarity threshold.

In S15, the microwave radar is controlled to send a second detection signal to the object to be detected, a heart rate waveform signal is extracted from the returned second detection signal, and a heart rate is calculated and recorded according to the heart rate waveform signal, till the next ranging signal needs to be sent.

Specifically, the heart rate waveform signal is extracted from the returned second detection signal by means of the phase demodulation principle of radar, and the heart rate is calculated and recorded according to the heart rate waveform signal. The process is repeated to calculate heart rate data for that period of time until the next ranging signal needs to be sent. After the ranging signal is sent again, it is determined whether the user is awake or continues to sleep according to the above step processes, and the subsequent steps are not performed if the user is awake, till the user is monitored to be in a sleep state. After the above processes, the user's heart rate data from falling asleep to waking up can be monitored and recorded.

In this embodiment of the present invention, the method includes: controlling the microwave radar to send a first detection signal to the human body when the microwave radar detects that the human body is not moving, and extracting a respiration waveform signal from the returned first detection signal; comparing the similarity of the respiration waveform signal and at least one respiration waveform signal standard sample in a sleep state in a preset respiration waveform signal database to obtain a similarity comparison result; determining that the object to be detected is currently in the sleep state if a similarity value in the similarity comparison result is greater than a preset similarity threshold, and controlling the microwave radar to send a second detection signal to the object to be detected; and extracting a heart rate waveform signal from the returned second detection signal, and calculating and recording a heart rate according to the heart rate waveform signal. It can thus be seen that the method, apparatus and system of the embodiments can perform non-contact monitoring on the heart rate after a user enters the sleep state, such that the user understands the heart rate health in his/her sleep state.

As an improvement of the present application, S13 further includes the following steps S130 to S133.

In S130, a target waveform segment of a preset length is determined from the respiration waveform signal.

Specifically, the waveform length of the extracted respiration waveform signal will be relatively long, which is not suitable for the analysis of the entire respiration waveform signal, otherwise the amount of data that needs to be analyzed will be relatively large, resulting in the following entire data analysis process being more time-consuming and untargeted. Therefore, the target waveform segment of the preset length may be determined from the respiration waveform signal. When the change in respiration frequency in the respiration waveform signal between the start of a data point and the following number of data points is less than a threshold (that is, the respiration frequency is uniform) and the respiration frequency is in a predetermined frequency interval (that is, in a slower respiration frequency interval, corresponding to the sleep state), this waveform is determined as the target waveform segment. For example, when the fifth data point to the fifteenth data point in the respiration waveform signal accord with the above situation, the waveform with a length of 10 is determined to be the target waveform segment.

In S131, sliding interception is performed on the target waveform segment according to a preset interception frame width, and a ratio of an amplitude difference between a maximum amplitude and a minimum amplitude of the waveform segment in each interception frame to a width of the interception frame is calculated as a first ratio of each interception frame of the target waveform segment.

A ratio of the amplitude difference between the maximum amplitude and the minimum amplitude of the waveform segment in each interception frame to the width of the interception frame can characterize a curve morphological change of each intercepted band of the respiration waveform, such that the similarity between bands can be compared by analyzing the similarity of the curve morphological change.

In S132, sliding interception is performed on the respiration waveform signal standard sample in each sleep state in the preset respiration waveform signal database according to the preset interception frame width, and a ratio of an amplitude difference between a maximum amplitude and a minimum amplitude of the waveform segment in each interception frame to the width of the interception frame is calculated as a second ratio of each interception frame of the respiration waveform signal standard sample, a waveform length of each respiration waveform signal standard sample being the preset length.

In S133, the similarity of the target waveform segment and each respiration waveform signal standard sample in the respiration waveform signal database is calculated by using a similarity algorithm based on the first ratio of each interception frame of the target waveform segment and the second ratio of the corresponding interception frame of each respiration waveform signal standard sample.

Specifically, according to a respiration waveform similarity comparison method of this embodiment, it is necessary to directly extract features that reflect the waveform morphological change from the original respiration waveform and amplify the change trend of important feature points such as a waveform inflection point, instead of extracting important feature information of the respiration waveform by means of such as a wavelet transform method to form a feature vector of similarity analysis. Therefore, the similarity between respiration waveforms can be analyzed more accurately while reducing dimensionality. By performing sliding interception on the respiration waveform segment according to the preset interception frame width and calculating the ratio of the amplitude difference between the maximum amplitude and the minimum amplitude of the waveform segment in each interception frame to the width of the interception frame, the changes of relevant respiration waveforms in different band morphologies are reflected. If the two respiration waveform segments are similar, the changes of the two respiration waveform segments in different band morphologies should also be similar. By using this principle, the similarity of the target waveform segment and each respiration waveform signal standard sample in the respiration waveform signal database may be calculated accurately. It should be noted that the value of the interception frame width cannot be too large or too small. If the value of the interception frame is too small, the amount of data that needs to be analyzed will be large and it is difficult to accurately reflect the change in band morphology; and if the value of the interception frame is too large, changes in some details of the waveform may be ignored, which will affect the accuracy of similarity analysis. As an example, the interception frame width is 0.1-0.2 of the waveform length of the target waveform segment. From the above analysis, it can be seen that the similarity calculation process of the respiration waveform signal in this embodiment does not need to be applied to a complex algorithm to extract feature information of the respiration waveform, and the entire calculation process is relatively, simple and occupies less computing resources.

Exemplarily, the similarity algorithm is as follows:

$$w_{AB} = \frac{1}{1+d}$$

wherein $w_{AB}$ is the similarity; d is a distance of the similarity, $$d = \sqrt{\sum_{i=1}^{n}(x_i - y_i)^2} \; ;$$

$x_i$ is a first ratio of the $i^{th}$ interception frame of the target waveform segment; $y_i$ is a second ratio of the $i^{th}$ interception frame of each respiration waveform signal standard sample; and n is the number of intercepted interception frames.

Specifically, the value of similarity $w_{AB}$ ranges from 0 to 1. The larger the value, the smaller d, that is, the closer to d, the greater the similarity. As an example, the similarity threshold is 0.8.

As an improvement of the present application, after calculating the heart rate according to the heart rate waveform signal, the method further includes:

judging whether the calculated heart rate exceeds a preset heart rate safety value range;

determining that a heart health status of the object to be detected is an abnormal heart rate if the calculated heart rate exceeds the preset heart rate safety value range; and determining that the heart health status of the object to be detected is a normal heart rate if the calculated heart rate does not exceed the preset heart rate safety value range.

In this embodiment, the abnormality of the user's heart rate is monitored by comparing whether the heart rate exceeds the preset heart rate safety value range.

As an improvement of the present application, after determining that the heart health status of the object to be detected is the abnormal heart rate, the method further includes:

sending prompt information to a user terminal or controlling a voice prompt apparatus to send a warning sound to the user.

In this embodiment, after the abnormality of the user's heart rate is monitored, the prompt information is sent to the user terminal or the voice prompt apparatus is controlled to send the warning sound to make a prompt for the user in time.

Figure 2:
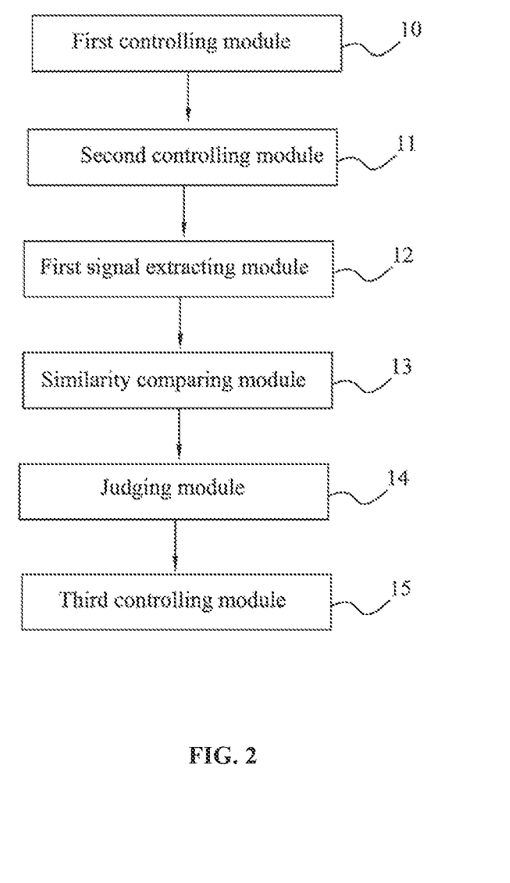
FIG. 2 is a schematic structural diagram of an apparatus for monitoring a heart rate in a sleep state based on a microwave radar according to an embodiment of the present invention.

FIG. 2 is a schematic structural diagram of an apparatus for monitoring a heart rate in a sleep state based on a microwave radar according to an embodiment of the present invention. The apparatus includes:

a first controlling module 10, configured to control the microwave radar to regularly send ranging signals to surrounding objects to be detected, and calculating a distance between the microwave radar and the object to be detected based on a returned ranging signal;

a second controlling module 11, configured to control the microwave radar to send a first detection signal to the object to be detected when a difference between the currently calculated distance and a distance calculated at the previous moment is less than a preset distance difference;

a first signal extracting module 12, configured to extract a respiration waveform signal from the returned first detection signal;

a similarity comparing module 13, configured to compare the similarity of the respiration waveform signal and at least one respiration waveform signal standard sample in a sleep state in a preset respiration waveform signal database to obtain a similarity comparison result;

a judging module 14, configured to determine that the object to be detected is currently in the sleep state if a similarity value in the similarity comparison result is greater than a preset similarity threshold; and a third controlling module 15, configured to control the microwave radar to send a second detection signal to the object to be detected, extract a heart rate waveform signal from the returned second detection signal, and calculate and record a heart rate according to the heart rate waveform signal, till the next ranging signal needs to be sent.

In this embodiment of the present invention, the method includes: controlling the microwave radar to send a first detection signal to an object to be detected when the microwave radar detects that the object to be detected is not moving, and extracting a respiration waveform signal from a returned first detection signal; comparing the similarity of the respiration waveform signal and at least one respiration waveform signal standard sample in a sleep state in a preset respiration waveform signal database to obtain a similarity comparison result; determining that the object to be detected is currently in the sleep state if a similarity value in the similarity comparison result is greater than a preset similarity threshold, and controlling the microwave radar to send a second detection signal to the object to be detected; and extracting a heart rate waveform signal from the returned second detection signal, and calculating and recording a heart rate according to the heart rate waveform signal. It can thus be seen that the method, apparatus and system of the embodiments can perform non-contact monitoring on the heart rate after a user enters the sleep state, such that the user understands the heart rate health in his/her sleep state.

As an improvement of the present application, the similarity comparing module is specifically configured to:

determine a target waveform segment of a preset length from the respiration waveform signal;

perform sliding interception on the target waveform segment according to a preset interception frame width, and calculate a ratio of an amplitude difference between a maximum amplitude and a minimum amplitude of the waveform segment in each interception frame to a width of the interception frame as a first ratio of each interception frame of the target waveform segment;

perform sliding interception on the respiration waveform signal standard sample in each sleep state in the preset respiration waveform signal database according to the preset interception frame width, and calculate a ratio of an amplitude difference between a maximum amplitude and a minimum amplitude of the waveform segment in each interception frame to the width of the interception frame as a second ratio of each interception frame of the respiration waveform signal standard sample, a waveform length of each respiration waveform signal standard sample being the preset length; and calculate the similarity of the target waveform segment and each respiration waveform signal standard sample in the respiration waveform signal database by using a similarity algorithm based on the first ratio of each interception frame of the target waveform segment and the second ratio of the corresponding interception frame of each respiration waveform signal standard sample.

As an improvement of the present application; the similarity algorithm is as follows:

$$w_{AB} = \frac{1}{1+d}$$

wherein $w_{AB}$ is the similarity; d is a distance of the similarity, $$d = \sqrt{\sum_{i=1}^{n}(x_i - y_i)^2};$$

$x_i$ is a first ratio of the $i^{th}$ interception frame of the target waveform segment; $y_i$ is a second ratio of the $i^{th}$ interception frame of each respiration waveform signal standard sample; and n is the number of intercepted interception frames.

As an improvement of the present application, the apparatus further includes:

a determining module; configured to determine whether the calculated heart rate exceeds a preset heart rate safety value range;

a first determining module; configured to determine that a heart health status of the object to be detected is an abnormal heart rate if the calculated heart rate exceeds the preset heart rate safety value range; and a second determining module, configured to determine that the heart health status of the object to be detected is a normal heart rate if the calculated heart rate does not exceed the preset heart rate safety value range.

As an improvement of the present application, the apparatus further includes:

a prompt module; configured to send prompt information to a user terminal or control a voice prompt apparatus to send a warning sound to the user.

Figure 3:
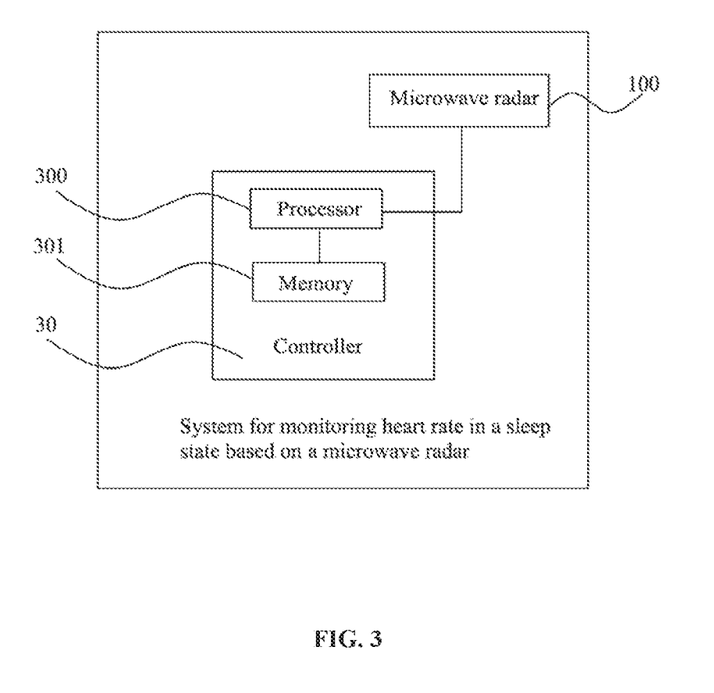
FIG. 3 is a schematic structural diagram of a system for monitoring a heart rate in a sleep state based on a microwave radar according to an embodiment of the present invention.

FIG. 3 is a schematic diagram of a system for monitoring a heart rate in a sleep state based on a microwave radar according to an embodiment of the present invention. The system for monitoring the heart rate in the sleep state based on the microwave radar in this embodiment includes the microwave radar 100, and a controller 30 connected to the microwave radar 100 and configured to control the microwave radar to operate. The controller 30 includes a processor 300, a memory 301, and a computer program that is stored in the memory 301 and configured to operate on the processor 300, for example, a heart rate monitoring program in the sleep state based on the microwave radar. The processor 300, when executing the computer program, implements the steps in the embodiments of the above-mentioned various methods for monitoring the heart rate in the sleep state based on the microwave radar. Alternatively, the processor 300, when executing the computer program, implements the functions of various modules/units in various apparatus embodiments.

Exemplarily, the computer program may be divided into one or more modules/units, the one or more modules/units being stored in the memory, and executed by the processor to accomplish the present invention. The one or more modules/units may be a series of computer program instruction segments capable of accomplishing a particular function, the instruction segments being configured to describe an execution process of the computer program in the system for monitoring the heart rate in the sleep state based on the microwave radar.

The system for monitoring the heart rate in the sleep state based on the microwave radar may include, but is not limited to, a processor and a memory. Those skilled in the art may understand that the schematic diagram is only an example of the system for monitoring the heart rate in the sleep state based on the microwave radar, without constituting a limitation on the system for monitoring the heart rate in the sleep state based on the microwave radar, and may include more or fewer components than shown, or a combination of certain components or different components. For example, the system for monitoring the heart rate in the sleep state based on the microwave radar may further include an input/output device, a network access device, a bus, etc.

The processor may be a CPU (Central Processing Unit), a universal processor, a DSP (Digital Signal Processor), an ASIC (Application Specific Integrated Circuit), an FPGA (Field-Programmable Gate Array), or other programmable logic devices, discrete gates or transistor logic devices, discrete hardware components, or the like. The universal processor may be a microprocessor or the processor may be any conventional processor, etc. The processor is a control center of the system for monitoring the heart rate in the sleep state based on the microwave radar, which uses various interfaces and circuits to connect various parts of the entire system for monitoring the heart rate in the sleep state based on the microwave radar.

The memory may be configured to store the computer program and/or module, and the processor implements various functions of the system for monitoring the heart rate in the sleep state based on the microwave radar by operating or executing the computer program and/or module stored in the memory and calling the data stored in the memory. The memory may mainly include a program storage area and a data storage area. The program storage area may store application programs required by an operating system and at least one function (e.g., a sound playback function or an image playback function). The data storage area may store data (e.g., audio data, and a telephone book) created based on the use of a smart phone. In addition, the memory may include a high-speed random access memory, and may further include a non-volatile memory, such as a hard disk, an internal storage, a pluggable hard disk, an SMC (Smart Media Card), an SC (Secure Digital) card, a flash card, at least one magnetic disk storage device, a flash memory device, or other non-volatile solid-state storage devices.

The modules/units integrated in the system for monitoring the heart rate in the sleep state based on the microwave radar, if implemented in the form of a software functional unit and sold or used as a separate product, may be stored in a computer-readable storage medium, Based on this understanding, the present invention implements all or part of the processes in the method embodiment, and may also be accomplished by a computer program to instruct relevant hardware. The computer program may be stored in a computer-readable storage medium. The computer program, while being executed by the processor, can implement the steps of various method embodiments. The computer program includes computer program codes, wherein the computer program codes may be in the form of source codes, object codes, executable files or some intermediate forms, etc. The computer-readable medium may include: any entity or apparatus capable of carrying the computer program codes, a recording medium, a U disk, a portable hard disk, a magnetic disk, an optical disk, a computer memory, an ROM (Read-Only Memory), an RAM (Random Access Memory), an electrical carrier signal, a telecommunications signal, a software distribution medium, etc. It should be noted that the content contained in the computer-readable medium may be appropriately increased or decreased according to the requirements of legislation and patent practice in the jurisdiction. For example, in some jurisdictions, according to legislation and patent practice, the computer-readable medium does not include electrical carrier signals and telecommunications signals.

It should be noted that the apparatus embodiments described above are merely, illustrative, wherein the units described as separate components may or may not be physically separated. The components displayed as units may or may not be physical units, i.e., may be located in one place, or may also be distributed on a plurality of network units. Part or all of the modules can be selected according to actual needs to achieve the object of the solution of this embodiment. Further, in the accompanying drawings of the apparatus embodiment provided by the present invention, the connection relationship between modules indicates a communication connection therebetween, which may be implemented as one or more communication buses or signal lines. Those of ordinary skill in the art can understand and implement the present invention, without paying any creative work.

The above description is only preferred embodiments of the present invention, and it should be noted that those of ordinary skill in the art may also make several improvements and modifications without departing from the principles of the present invention, which should be considered as the protection scope of the present invention.

The invention claimed is:

1. A method for monitoring a heart rate in a sleep state based on a microwave radar, comprising:
controlling the microwave radar to regularly send ranging signals to an object to be detected, and calculating a distance between the microwave radar and the object to be detected based on the returned ranging signals;
controlling the microwave radar to send a first detection signal to the object to be detected when a difference between the currently calculated distance and a distance calculated at the previous moment is less than a preset distance difference;

extracting a respiration waveform signal from the first detection signal;

comparing similarity of the respiration waveform signal and at least one respiration waveform signal standard sample in the sleep state in a preset respiration waveform signal database to obtain a similarity comparison result;

determining that the object to be detected is currently in the sleep state if a similarity value in the similarity comparison result is greater than a preset similarity threshold; and controlling the microwave radar to send a second detection signal to the object to be detected, extracting a heart rate waveform signal from the second detection signal, and calculating and recording the heart rate according to the heart rate waveform signal, till the next ranging signal needs to be sent, wherein said comparing the similarity of the respiration waveform signal and the at least one respiration waveform signal standard sample in the sleep state in the preset respiration waveform signal database to obtain the similarity comparison result comprises:

determining a target waveform segment of a preset length from the respiration waveform signal;

performing sliding interception on the target waveform segment according to a preset interception frame width, and calculating a ratio of an amplitude difference between a maximum amplitude and a minimum amplitude of the waveform segment in each interception frame to a width of each interception frame as a first ratio of each interception frame of the target waveform segment;

performing sliding interception on the respiration waveform signal standard sample in each sleep state in the preset respiration waveform signal database according to the preset interception frame width, and calculating another ratio of another amplitude difference between another maximum amplitude and another minimum amplitude of another waveform segment in each interception frame to the width of the interception frame as a second ratio of each interception frame of the respiration waveform signal standard sample, a waveform length of each respiration waveform signal standard sample being the preset length; and calculating the similarity of the target waveform segment and each respiration waveform signal standard sample in a respiration waveform signal database by using a similarity algorithm based on the first ratio of each interception frame of the target waveform segment and the second ratio of the corresponding interception frame of each respiration waveform signal standard sample;

the similarity algorithm being as follows:

$$w_{AB} = \frac{1}{1+d}$$

wherein $w_{AB}$ is the similarity; d is a distance of the similarity;

$$d = \sqrt{\sum_{i=1}^{n}(x_i - y_i)^2},$$

$x_i$ is another first ratio of the $i^{th}$ interception frame of the target waveform segment, $y_i$ is another second ratio of $i^{th}$ the interception frame of each respiration waveform signal standard sample, and n is the number of intercepted interception frames.

2. The method according to claim 1, after calculating and recording the heart rate according to the heart rate waveform signal, the method further comprising:

judging whether the calculated heart rate exceeds a preset heart rate safety value range;

determining that a heart health status of the object to be detected is an abnormal heart rate if the calculated heart rate exceeds the preset heart rate safety value range; and determining that the heart health status of the object to be detected is a normal heart rate if the calculated heart rate does not exceed the preset heart rate safety value range.

3. The method according to claim 2, after determining that the heart health status of the object to be detected is the abnormal heart rate, the method further comprising:

sending prompt information to a user terminal or controlling a voice prompt apparatus to send a warning sound to the user.

4. An apparatus for monitoring a heart rate in a sleep state based on a microwave radar, comprising:

a first controlling module, configured to control the microwave radar to regularly send ranging signals to an object to be detected, and calculating a distance between the microwave radar and the object to be detected based on a returned ranging signal;

a second controlling module, configured to control the microwave radar to send a first detection signal to the object to be detected when a difference between a currently calculated distance and a distance calculated at a previous moment is less than a preset distance difference;

a first signal extracting module, configured to extract a respiration waveform signal from the first detection signal;

a similarity comparing module, configured to compare similarity of the respiration waveform signal and at least one respiration waveform signal standard sample in the sleep state in a preset respiration waveform signal database to obtain a similarity comparison result;

a determining module, configured to determine that the object to be detected is currently in the sleep state if a similarity value in the similarity comparison result is greater than a preset similarity threshold; and a third controlling module, configured to control the microwave radar to send a second detection signal to the object to be detected, extracting a heart rate waveform signal from the returned second detection signal, and calculating and recording a heart rate according to the heart rate waveform signal, till the next ranging signal needs to be sent;

the similarity comparing module being specifically configured to:

determine a target waveform segment of a preset length from the respiration waveform signal;

perform sliding interception on the target waveform segment according to a preset interception frame width, and calculating a ratio of an amplitude difference between a maximum amplitude and a minimum amplitude of the waveform segment in each interception frame to a width of the interception frame as a first ratio of each interception frame of the target waveform segment;
perform sliding interception on the respiration waveform signal standard sample in each sleep state in the preset respiration waveform signal database according to the preset interception frame width, and calculate another ratio of another amplitude difference between another maximum amplitude and another minimum amplitude of another waveform segment in each interception frame to the width of the interception frame as a second ratio of each interception frame of the respiration waveform signal standard sample, a waveform length of each respiration waveform signal standard sample being the preset length; and
calculate the similarity of the target waveform segment and each respiration waveform signal standard sample in the respiration waveform signal database by using a similarity algorithm based on the first ratio of each interception frame of the target waveform segment and the second ratio of the corresponding interception frame of each respiration waveform signal standard sample;
the similarity algorithm being as follows:

$$w_{AB} = \frac{1}{1+d}$$

wherein $w_{AB}$ is the similarity; d is a distance of the similarity, $$d = \sqrt{\sum_{i=1}^{n}(x_i - y_i)^2},$$

$x_i$ is another first ratio of the $i^{th}$ interception frame of the target waveform segment, $y_i$ is another second ratio of the $i^{th}$ interception frame of each respiration waveform signal standard sample, and n is the number of intercepted interception frames.

5. The apparatus according to claim 4, comprising:
a judging module, configured to judge whether the calculated heart rate exceeds a preset heart rate safety value range;
a first determining module, configured to determine that a heart health status of the object to be detected is an abnormal heart rate if the calculated heart rate exceeds the preset heart rate safety value range; and
a second determining module, configured to determine that the heart health status of the object to be detected is a normal heart rate if the calculated heart rate does not exceed the preset heart rate safety value range.

6. A system for monitoring the heart rate in the sleep state based on the microwave radar, comprising the microwave radar, and a controller connected to the microwave radar and configured to control the microwave radar to operate, wherein
the controller comprises a processor, a memory, and a computer program that is stored in the memory and configured to be executed by the processor, wherein the processor is configured to implement the method for monitoring the heart rate in the sleep state based on the microwave radar according to claim 1 when executing the computer program.

7. A system for monitoring the heart rate in the sleep state based on the microwave radar, comprising the microwave radar, and a controller connected to the microwave radar and configured to control the microwave radar to operate, wherein
the controller comprises a processor, a memory, and a computer program that is stored in the memory and configured to be executed by the processor, wherein the processor is configured to implement the method for monitoring the heart rate in the sleep state based on the microwave radar according to claim 2 when executing the computer program.

8. A system for monitoring the heart rate in the sleep state based on the microwave radar, comprising the microwave radar, and a controller connected to the microwave radar and configured to control the microwave radar to operate, wherein
the controller comprises a processor, a memory, and a computer program that is stored in the memory and configured to be executed by the processor, wherein the processor is configured to implement the method for monitoring the heart rate in the sleep state based on the microwave radar according to claim 3 when executing the computer program.

9. A computer-readable storage medium, comprising a computer program stored therein, wherein the computer program, when in operation, controls a device where the computer-readable storage medium is located to perform the method for monitoring the heart rate in the sleep state based on the microwave radar according to claim 1.

10. A computer-readable storage medium, comprising a computer program stored therein, wherein the computer program, when in operation, controls a device where the computer-readable storage medium is located to perform the method for monitoring the heart rate in the sleep state based on the microwave radar according to claim 2.

11. A computer-readable storage medium, comprising a computer program stored therein, wherein the computer program, when in operation, controls a device where the computer-readable storage medium is located to perform the method for monitoring the heart rate in the sleep state based on the microwave radar according to claim 3.

\* \* \* \* \*